United States Patent [19]
Dragan et al.

[11] Patent Number: 5,871,355
[45] Date of Patent: Feb. 16, 1999

[54] DENTAL MIXING CAPSULE FOR DISPENSING A MULTIPLE COMPONENT DENTAL MATERIAL

[75] Inventors: William B. Dragan, Easton; Gordon Rowe, Wallingford, both of Conn.

[73] Assignee: Centrix, Inc., Shelton, Conn.

[21] Appl. No.: 924,670

[22] Filed: Sep. 5, 1997

[51] Int. Cl.⁶ ............................................. A61C 5/04
[52] U.S. Cl. ........................................................ 433/90
[58] Field of Search ........................... 206/219, 221, 206/63.5; 433/89, 90; 604/222, 226, 229

[56] References Cited

U.S. PATENT DOCUMENTS

| | | | |
|---|---|---|---|
| Re. 33,801 | 1/1992 | Green | 222/82 |
| 2,773,591 | 12/1956 | Jensen . | |
| 3,425,598 | 2/1969 | Kobernick | 206/222 |
| 3,595,439 | 7/1971 | Newby et al. | 222/80 |
| 3,684,136 | 8/1972 | Baumann | 222/386 |
| 3,739,947 | 6/1973 | Baumann et al. | 222/136 |
| 3,974,831 | 8/1976 | Malmin | 604/222 |
| 4,515,267 | 5/1985 | Welsh | 206/219 |
| 4,941,751 | 7/1990 | Muhlbauer | 206/219 |
| 5,026,283 | 6/1991 | Osanai et al. | 433/90 |
| 5,052,927 | 10/1991 | Discko, Jr. | 433/90 |
| 5,172,807 | 12/1992 | Dragan et al. | 206/219 |

FOREIGN PATENT DOCUMENTS

| | | | |
|---|---|---|---|
| 651250 | 5/1993 | Australia | 433/89 |

*Primary Examiner*—Cary E. O'Connor
*Attorney, Agent, or Firm*—Fattibene & Fattibene; Arthur T. Fattibene; Paul A. Fattibene

[57] ABSTRACT

A dental capsule that requires a capsule body defining a reservoir that is loaded with predetermined amounts of one or more materials to be mixed, sealed by a removable plug having flexible gripping flange fingers extending laterally relative to the axis of the capsule to facilitate the removal of the plug. Subsequent to the mixing of the materials within the capsule by amalgamation, the capsule is placed in a suitable ejector or syringe whereby the mixed materials can be readily extruded therefrom and directly placed in or about a prepared tooth whereby the flexible gripping flange fingers function as a base for storing the capsule in a vertical position and which flexible fingers are capable of being deflected so as to be pushed through the capsule as the plug is displaced to extrude the mixed material.

8 Claims, 2 Drawing Sheets

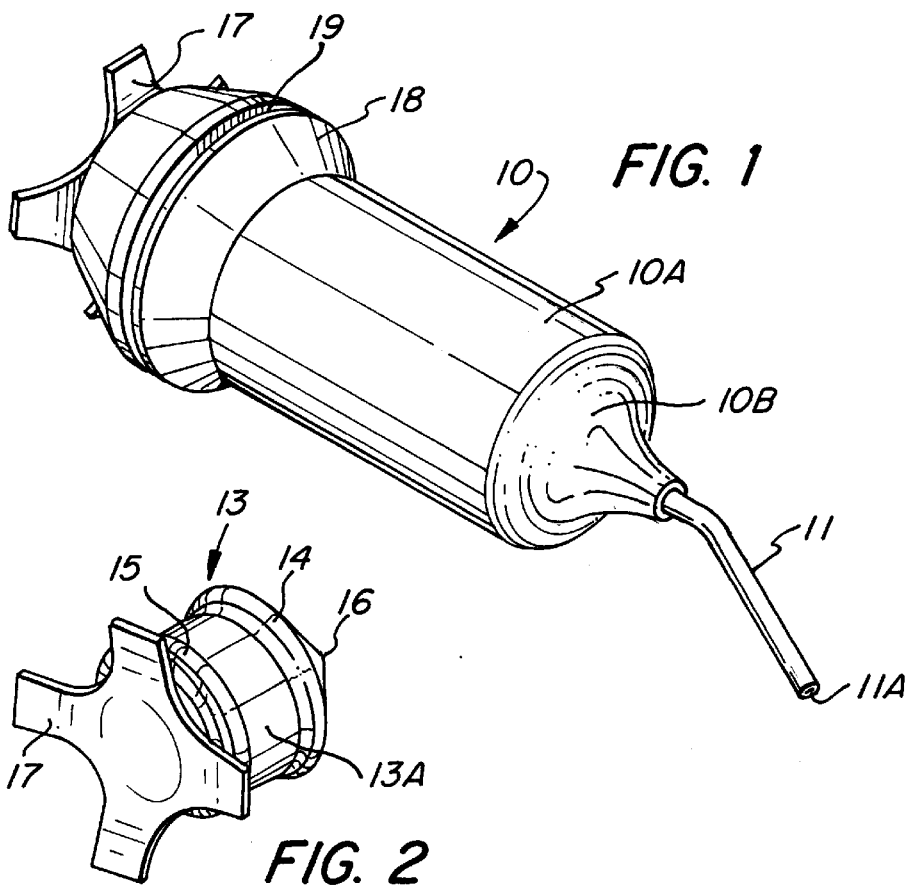
FIG. 1
FIG. 2
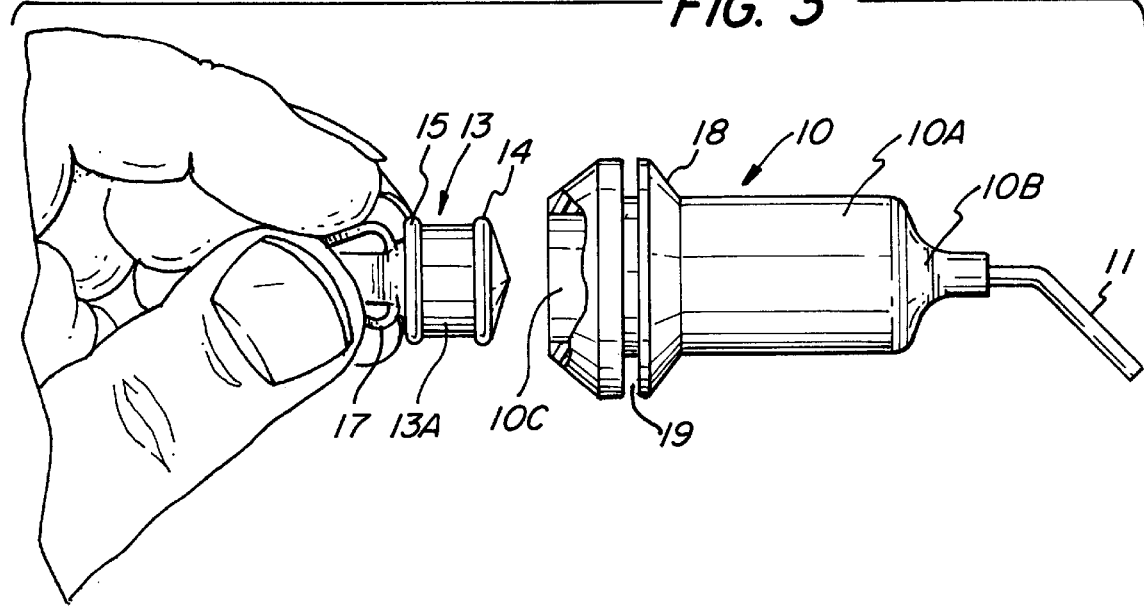
FIG. 3

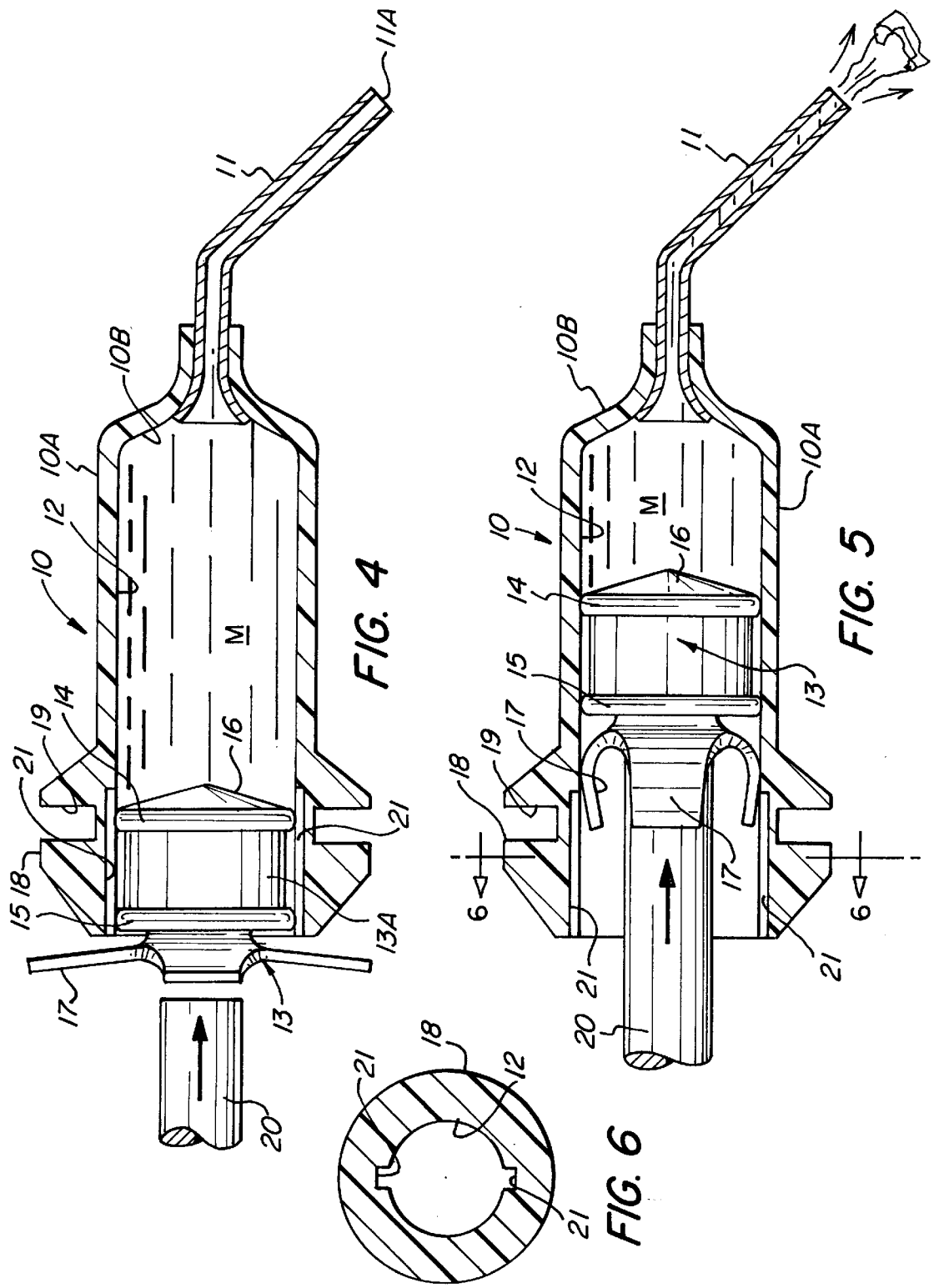

DENTAL MIXING CAPSULE FOR DISPENSING A MULTIPLE COMPONENT DENTAL MATERIAL

FIELD OF THE INVENTION

The invention relates to a dental capsule and method for mixing at least two predetermined amounts of material therein to form a uniform mixture immediately prior to use and dispensing therefrom the mixed material.

BACKGROUND OF THE INVENTION

In dentistry, it is common to use various dental materials such as cements, impression materials, composites and the like which consist of two or more parts, one of which includes an activating ingredient that initiates a chemical reaction when the non-activated material or part is mixed with the activating ingredient or part to render the mixed material operative for effecting the dental procedure. Heretofore, such dental materials were separately packaged in bulk containers from which a dentist would dispense a predetermined amount of said materials or ingredients onto a pad and manually mix the dispensed amounts by hand to form a homogeneous mass. Thereafter, the dentist would apply the homogeneous mass with a spatula or other suitable hand instrument.

To eliminate the tedious effort of hand mixing such dental material and the waste incidental to such manual mixing, efforts have been made to package such materials into a capsule with predetermined measured amounts of the respective non-activated and activating materials. In such efforts, it was necessary to construct the capsule so that the respective ingredients are maintained separated one from the other therein until ready to be mixed. The constructions of such known capsules comprise relatively complex arrangements and/or structures that are costly and complex to manufacture and/or load. Illustrative examples of such known prior efforts are disclosed in U.S. Pat. Nos. 2,273,591; 3,425,598; 3,595,439; 3,684,136; 3,739,947; 4,515,267; 4,941,751; 5,026,283; RE 33,801 and 5,172,807.

SUMMARY OF THE INVENTION

An object of this invention is to provide an improved dental capsule and method for mixing two or more dental materials to form a homogeneous mixture thereof prior to use which is relatively simple in structure and easy to manufacture.

Another object is to provide a combined mixing and dispensing capsule which can be readily preloaded by a dentist at chair side and/or preloaded by the manufacturer with at least one of the materials, with the other material being added thereto by the dentist at chair side prior to mixing.

Another object is to provide a dental mixing capsule with an improved plug arranged so as to be readily removable from the capsule either before or after the capsule has been loaded with a dental material.

The foregoing objects are obtained by a capsule having a body portion defining a reservoir for containing the dental materials to be mixed. One end of the reservoir is closed by an end wall through which a nozzle or cannula is extended to define a discharging nozzle. The nozzle or cannula is preferably formed of a ductile material which can be readily bent to define a suitable angle to facilitate the placement of the material during an extruding operation in performing a dental procedure.

The other end of the capsule or reservoir defines an open end which is sealed by a piston or plug; which, when displaced, forces the material within the capsule to extrude through the nozzle. The piston or plug includes a cylindrical portion having one or more circumscribing sealing rings to define a seal between the piston and the internal bore or reservoir of the capsule. The end of the plug is provided with a radial extending flexible flange or flange fingers to provide a gripping means whereby the plug can be readily pulled free of the capsule. The flange or flange fingers are sufficiently flexible so as to be pushed through the capsule as the plug is displaced to extrude the mixed material.

Circumscribing the open end of the capsule is a laterally extending collar having a circumscribing groove formed therein to facilitate the attachment thereof in an extruding device or syringe to effect the extrusion of the mixed material therefrom.

The arrangement is such that the capsule can be readily loaded by the dentist at chair side with predetermined amounts of the respective materials to be mixed. As an alternative, the capsule may be preloaded with one of the ingredients and sealed by the plug at the point of manufacture by the manufacturer, and the dentist, at chair side, can add thereto the activating ingredient prior to mixing.

A feature of this invention is to provide a relatively simple mixing capsule construction which can be readily loaded either by the dentist and/or by the manufacturer with at least one of the ingredients which can be readily supplemented by the dentist at chair side with the other ingredient or ingredients prior to mixing.

Other features and advantages will become more readily apparent in view of the following description.

IN THE DRAWINGS

FIG. 1 is a perspective view of a dental mixing capsule embodying the invention.

FIG. 2 is a perspective view of the sealing plug for use with the capsule of FIG. 1.

FIG. 3 is a side view of the capsule and plug of FIGS. 1 and 2 illustrating the manner of removal.

FIG. 4 is a sectional side view of the capsule in a normal inoperative position.

FIG. 5 is a sectional side view of the capsule in an intermediate operative position.

FIG. 6 is a sectional view taken along line 6—6 on FIG. 5.

DETAILED DESCRIPTION

Referring to the drawings, there is shown a dental capsule 10 embodying the invention. As shown, the dental capsule 10 includes a cylindrical body portion 10A which defines a reservoir 12 for receiving the dental materials to be mixed therein. One end of the capsule 10 is closed by an end wall 10B through which a discharge nozzle 11 in the form of a needle or cannula extends. The cannula or nozzle 11 is preferably formed of a ductal material which can be readily bent to define a suitable angle to facilitate the placement of the material extruded therefrom during a dental procedure. The needle or cannula defining the nozzle 11 is flared at the inner end thereof, as best seen in FIGS. 4 and 5. The arrangement is such that the needle or cannula forming the nozzle 11 can be rotated a full 360° relative to the body 10A of the capsule in a manner as described in U.S. Letters Pat. No. 5,336,088 granted Aug. 9, 1994.

The other end of the capsule 10 is provided with a full open end 10C which is arranged to be sealed by an end plug or piston 13. As shown, the end plug or piston is provided with a cylindrical body portion 13A which has a diameter sized to be received within the reservoir 12 defined within the capsule 10. Circumscribing about the outer periphery of the body portion 13A of the plug 13 are one or more sealing rings 14, 15.

In the illustrative embodiment, the sealing rings 14 and 15 are spaced apart and circumscribe the body portion 13A at the front and rear thereof. The front end 16 of the plug 13 is generally shaped to conform to that of the end wall 10B of the capsule 10 so as to ensure maximum extrusion of the material M within the capsule 13. It will be understood that the sealing rings 14 and 15 are disposed in snug, sliding relationship to the interior bore or walls of the reservoir 12 to form a seal thereat as the plug or piston 13 is displaced longitudinally of the reservoir 12.

In accordance with this invention, the outer end of the plug or piston is provided with a laterally, outwardly extending flexible flange or flexible fingers 17 that are integrally formed on the plug or piston 13. Preferably, the plug 13 is formed of a rubberlike material or suitable flexible plastic material. As shown in FIGS. 1 and 4, the flexible flange or fingers 17 extend radially outward beyond the circumference of the capsule body 10A to provide a gripping means whereby the plug or piston 13 can be readily pulled free of the capsule body 10A as best seen in FIG. 3.

Circumscribing the open end 10C of the capsule is a laterally extending flange or collar 18 having a circumscribing groove 19 intermediate the width of the collar or flange 18.

The capsule 13 described is particularly useful for packaging and/or dispensing dental materials which are comprised of multiple components that are required to be mixed before they can be used. Generally, such dental materials include an inactive and an active component which are required to be maintained separate or out of contact with one another until ready for use. Certain impression materials comprised of two components which react when mixed. Also, certain dental cements are comprised of a powder component and a liquid component which are required to be mixed to form a usable cement. Heretofore, such materials were required to be mixed at chair side by the dentist and manually placed by means of a spatula or other suitable dental tool. Also, capsules have been developed in which the respective component ingredients were maintained in separate compartments within a common capsule and in which the component ingredients were mixed only after the separating compartments have been penetrated or fractured by piercing and/or the like.

The capsule 10 embodying the present invention can be either loaded by the dentist at chairside with the appropriate predetermined amounts of the respective ingredients and sealed by inserting the plug or piston 13 in the open end 10C of the capsule. With the component ingredients disposed within the reservoir 12, the loaded capsule is then placed in a suitable amalgamator or vibrating mixer whereby the ingredients are homogeneously mixed within the capsule 10 by the vibration imparted to the capsule 10. After mixing, the capsule 10 is placed in a suitable ejector or syringe of a type as described in U.S. Pat. No. 5,306,147 granted Apr. 26, 1994, and the material extruded by effecting the displacement of the piston or plug 13 by the syringe plunger 20.

As an alternate application, the capsule 10 may be preloaded by the manufacturer with a predetermined amount of a dental material, e.g. one part of a two-part impression material, or the powdered component of a dental cement or the like, and sealed therein by the plug or piston 13. Such preloaded capsule, when purchased by the dentist, is made ready for use by the dentist by the dentist removing the plug 13 by grasping the flange or flange fingers 17 to pull the plug free. The dentist at chairside would then add the activating or missing component to be combined with the preloaded ingredient, and resealing the capsule 10 by reinserting the plug 13. The capsule 10, thus loaded with the appropriate amount of the two or more respective ingredients, is placed in an amalgamator or vibrating mixer (not shown) for mixing to create a homogeneous or blended mixture. After mixing, the capsule 10 is placed in a suitable syringe, as hereinbefore described, whereby the dentist can directly dispense the mixture therefrom directly to the site of the tooth being worked upon.

To facilitate the insertion of the plug 13 into the open end 10C of the capsule 10, there is provided a vent. As best seen in FIGS. 4, 5 and 6, the vent is formed as a groove 21 which extends along the internal bore or reservoir 12 adjacent the open end 10C. The length of the venting groove 21 extends from the open end of the capsule to slightly beyond the end 16 of the plug 13, when the plug is properly seated, as best seen in FIG. 4. The arrangement is such that when the plug 13 is inserted into the open end 10C of the capsule to seal the same, the air within the capsule, which is displaced by the plug 13, is vented through the vent grooves 21. Two oppositely disposed venting grooves 21 are illustrated.

In displacing the piston or plug 13 to effect extrusion, the radially extending fingers 17 are deflected, as best seen in FIG. 5. The deflected fingers or flange 17 can thus be pushed through the capsule 10 as the plunger 20 of a syringe (not shown) causes the plug 13 to be displaced within the reservoir 12.

It will be apparent that the capsule 10 described constitutes a relatively simple structure in which two or more reactive dental ingredients can be readily mixed without the requirement of a relatively complex structure to maintain the ingredients separated until ready for use. The arrangement is such that the capsule 10 can be readily preloaded by the dentist at chair side with the respective predetermined amounts of the component materials, or the capsule may be partially preloaded by the manufacturer, and to which the dentist may add the missing component at chair side to be combined with the preloaded ingredient just prior to imparting a vibratory moment to the capsule 10 to effect the mixing of the materials within the capsule 10.

It will be understood that the volume of the reservoir can vary over a relatively large range. To render the capsule useful for making precision type impressions when loaded with a two-part impression material, the volume of the described capsules can vary in the range of 1.5 to 2.5 ML, which is some 7 to 15 times greater than the typical unit dose dental capsules.

In the event that the capsule 10, as herein described, is preloaded with a predetermined amount of a component part of a multiple component dental material, the discharge end 11A may be suitably sealed by a sealing cap, sealing pin and the like, in a well known manner to protect any contamination of the material M initially preloaded or packaged in the capsule.

The radially extending flexible flange or fingers 17 also provide a stable base for the capsules whereby the capsule can be stored upright in a vertical position until ready for use.

While the present invention has been described with respect to a particular embodiment and method, modifications and variations may be made without departing from the spirit or scope of this invention.

What is claimed is:

1. A dental capsule for mixing and dispensing a multiple component dental material comprising:

a capsule body defining a reservoir for containing a multiple component dental material, said reservoir having an end wall at one end and having an open end opposite said end wall, a discharge nozzle disposed in communication with said reservoir connected to said end wall, a displaceable plug sealing said open end, said plug having a cylindrical body and an inner and outer end portion, said plug having a plurality of flexible flange fingers connected to said outer end portion and extending laterally outwardly therefrom forming a base for storing the capsule in a vertical position, and said flexible flange fingers defining a grip for said plug to enable one to pull the plug free of said capsule body, and whereby said flange fingers deflect axially outwardly to engage the interior of said reservoir as said plug is displaced longitudinally of said reservoir during an extruding operation.

2. A dental capsule as defined in claim 1 and having an annular collar circumscribing said open end, said collar extending radially outwardly, and a circumscribing groove disposed intermediately the width of said collar.

3. A dental capsule as defined in claim 1 wherein said plug includes a sealing ring circumscribing said cylindrical body of said plug.

4. A dental capsule as defined in claim 1 wherein said reservoir has a capacity in the range of 1.5 to 2.5 milliliters.

5. A dental capsule as defined in claim 1 wherein said nozzle comprises a needle cannula, said cannula being formed of a ductile material whereby said cannula can be bent to a desired angle.

6. A dental capsule for mixing and dispensing a dental material formed of multiple component parts that require an intimate mixing prior to the use thereof comprising:

an elongated cylindrical capsule body defining a reservoir for containing the multiple component dental material, said capsule body having an end wall at one end thereof, and an open end opposite thereto, a needle cannula connected in communication with said reservoir being extended through said end wall, an outwardly extending radial collar circumscribing said capsule body adjacent said open end, a circumscribing groove formed intermediate the width of said collar, and a plug for sealing said open end, said plug including a cylindrical portion sized to be received within said reservoir, sealing ring circumscribing said plug, and a plurality of flexible flange fingers connected to the outer end of said plug, said flange fingers projecting laterally outwardly of said plug so as to extend beyond the circumference of said capsule body to provide a stable base for storing the dental capsule in a vertical position, said flange fingers defining a gripping means for effecting the ready removability of said plug, and whereby said flange fingers deflect axially outwardly to engage the interior of said reservoir as said plug is disposed longitudinally of said reservoir during an extruding operation.

7. A dental capsule as defined in claim 6 and including a predetermined amount of one component of a multiple component dental material sealed within said reservoir.

8. A dental capsule as defined in claim 6 and including a venting groove extending longitudinally of said capsule body internally thereof adjacent said open end.

* * * * *